(12) United States Patent
Wolf et al.

(10) Patent No.: US 6,277,629 B1
(45) Date of Patent: Aug. 21, 2001

(54) APPARATUS FOR MEASURING PHYSIOLOGICAL PARAMETERS

(75) Inventors: Bernhard Wolf, Stegen; Ulrich Sieben, Reute, both of (DE)

(73) Assignee: Micronas GmbH, Freiburg (DE)

( * ) Notice: Subject to any disclaimer, the term of this patent is extended or adjusted under 35 U.S.C. 154(b) by 0 days.

(21) Appl. No.: 09/585,178

(22) Filed: Jun. 1, 2000

Related U.S. Application Data

(63) Continuation of application No. PCT/EP98/07598, filed on Nov. 25, 1998.

(30) Foreign Application Priority Data

Dec. 3, 1997 (DE) .............................................. 197 53 598

(51) Int. Cl.[7] .................................................. C12M 1/34
(52) U.S. Cl. ..................... 435/288.3; 435/288.7; 435/305.1; 435/305.4; 435/808; 204/403; 324/446; 324/692; 356/246
(58) Field of Search .............. 435/287.1, 287.2, 435/288.3, 288.7, 289.1, 305.1, 808; 204/403; 324/446, 692; 356/246

(56) References Cited

U.S. PATENT DOCUMENTS

| | | | |
|---|---|---|---|
| 5,278,048 | 1/1994 | Parce et al. | 436/29 |
| 5,563,067 | 10/1996 | Sugihara et al. | 435/287.1 |
| 5,632,957 | 5/1997 | Heller et la. | 422/68.1 |
| 5,851,489 | * 12/1998 | Wolf et al. | 422/82.02 |

FOREIGN PATENT DOCUMENTS

| | | | |
|---|---|---|---|
| 44 17 079 A1 | 12/1995 | (DE) | G02B/21/34 |
| 0 611 598 A2 | 8/1994 | (EP) | B01L/7/00 |
| WO 94/05414 | 3/1994 | (WO) | B01F/11/02 |
| WO 96/32467 | 10/1996 | (WO) | C12M/1/34 |
| WO 97/44132 | 11/1997 | (WO) | B01L/3/00 |
| WO 98/50514 | 11/1998 | (WO) | B01L/3/00 |

* cited by examiner

Primary Examiner—David A. Redding
(74) Attorney, Agent, or Firm—Akin, Gump, Strauss, Hauer & Feld, L.L.P.

(57) ABSTRACT

An apparatus (1) for measuring physiological parameters has a test chamber (2) having boundaries defined by a first semiconductor chip (3) and a second semiconductor chip (4), between which chips a seal (7) bordering the test chamber (2) is arranged as a distance spacer. The first semiconductor chip (3) has an active side, which faces the test chamber (2) and has planar sensors, on which biological cells (6) located in a nutrient medium can be adherently deposited in order to measure physiological parameters directly on the cells (6). The second semiconductor chip (4) has on an active side, facing the test chamber (2), at least one additional sensor to measure global physiological parameters. The semiconductor chips (3, 4) are held in the sealing position using a mounting (8) that grasps over them on the outer side. Outside of the test chamber (2) the semiconductor chips (3, 4) each have electric connection contacts, which contact with opposing contacts of the mounting. The apparatus is constructed simply and cost-effectively.

16 Claims, 3 Drawing Sheets

APPARATUS FOR MEASURING PHYSIOLOGICAL PARAMETERS

CROSS-REFERENCE TO RELATED APPLICATION

This application is a continuation of International Application No. PCT/EP98/07598, filed Nov. 25, 1998, the disclosure of which is incorporated herein by reference.

BACKGROUND OF THE INVENTION

The invention relates to an apparatus for measuring physiological parameters, the apparatus having a test chamber connected to at least one inlet opening and at least one outlet opening and bordered by walls, wherein at least one wall of the test chamber is constructed as a semiconductor chip, which has an active side having planar sensors facing the test chamber, on which biological cells located in a nutrient medium can be adherently deposited, in order to measure physiological parameters directly on the cells, and wherein at least one additional sensor is allocated to a wall lying opposite the semiconductor chip in order to measure global physiological parameters.

Such an apparatus is already known from German published patent application DE 44 17 079 A1. It has a test chamber in which animal or plant biological cells can be kept vital in a nutrient medium over a long time period. There, the nutrient medium can be renewed through the inlet and outlet openings of the test chamber, for example using a fluid treatment. In the test chamber the cells are deposited adherently on the active side of the semiconductor chip having the planar sensors. For this purpose, the semiconductor chip can have, for example, on its active side a surface structuring, whose roughness corresponds approximately to the coarseness of the cells, so that they accept the semiconductor chip as neighbors and become better accumulated thereon.

The planar sensors allow an almost continuously flat chip surface, so that the cells can become deposited directly onto the planar sensors. It is thereby possible with the planar sensors to measure directly on the cells physical, electrical, or electrochemical cell parameters, for example ion concentrations, gas contents, cell potentials, or cell temperatures. Thus, the reaction of the cells can be tested in a simple manner for changed physical or chemical conditions, for example toxic substances, drugs, environmental toxins and the like contained in the nutrient medium. The cells thereby act as biological pre-amplifiers, which increase the measuring sensitivity of the planar sensors. Using the additional sensors allocated to the wall lying opposite the semiconductor chip, it is also possible to detect global physiological parameters in the nutrient medium. In this manner, additional information can be obtained about the cells.

Although the previously known apparatus has proven to be useful in practice, it nevertheless has disadvantages. It is still constructed in a comparatively complicated manner. The apparatus is therefore relatively expensive, which limits its usage possibilities.

SUMMARY OF THE INVENTION

Therefore, an object of the invention is to create an apparatus of the type mentioned at the outset, which is constructed in a simple and cost-effective manner.

This object is achieved in that the wall of the test chamber lying opposite the semiconductor chip is formed by a second semiconductor chip, which has an active side facing toward the test chamber and having at least the additional sensor, that a seal surrounding the test chamber is arranged as a distance spacer between the semiconductor chips, that the semiconductor chips are held in the sealing position using a mounting that grasps over them on the outside, and that the semiconductor chips each have electric connection contacts outside of the test chamber, which contact with the opposing contacts of the mounting.

Thus, all sensors of the apparatus can be integrated in the semiconductor chips, wherein the semiconductor chips form, at the same time, the boundary walls of the test chamber. In an advantageous manner, the seal arranged between the semiconductor chips also functions at the same time as a distance spacer, so that between the semiconductor chips a defined chamber volume is formed without having to have cavities in the semiconductor chips. The semiconductor chips can thus be constructed as cost-effective planar chips. It is also advantageous that the clearance distance between the semiconductor chips, and thus the height of the test chamber, is defined by the thickness of the seal. Thus, test chambers having different heights can be made with the same semiconductor chips, where respectively only the dimensions of the seal and, optionally those of the, must be fitted correspondingly. Thus, in a simple manner, a plurality of test chambers having different dimensions can be prepared. The opposing contacts provided on the mounting and acting together with the connection contacts of the semiconductor chips allow, in a simple manner, an electrical connection between the semiconductor chips bordering the test chamber and/or the semiconductor chips and an external evaluation unit or a power supply unit. On the whole, a biomonitor results which is simply constructed and can be manufactured cost-effectively.

It is advantageous if at least one inlet channel having the inlet opening and/or at least one outlet channel having the outlet opening penetrates the seal. The inlet and outlet channels of the test chamber are thus arranged in the seal, so that wall openings in the semiconductor chip can be omitted.

In an expedient manner, the seal comprises an elastic material and is preferably constructed as an O-ring. As an inlet or outlet channel, a hollow needle, for example, can then be provided which penetrates the seal. The apparatus can then be handled in an especially flexible manner.

A preferred embodiment of the invention provides that the mounting has at least one holding clip or a holding clamp with at least two clamping parts, which have a smaller clearance distance in the starting position than the total thickness of the semiconductors spaced from each other by the seal and to be clamped between the clamping parts, and that the clamping parts can be moved away from each other against a restoring force. The mounting can then be combined with seals having various thicknesses, such that the clearance distance between the clamping parts becomes fitted to the overall thickness of the parts, which are to be clamped between the clamping parts, which varies depending on the thickness of the seal. Consequently, in a simple manner, a plurality of test chambers can be prepared having various chamber heights, i.e., with various distances between the semiconductor chips. Optionally, the chamber height of the apparatus can also be changed later by replacing the seal with a thicker or thinner seal. Thus, for example, certain experimental techniques, such as the determination of the metabolic activity of cells by the measurement of the pH-value and the oxygen concentration, require a high cell count to chamber volume ratio or an extremely small chamber height. In other applications, on the other hand, a larger chamber height can be advantageous, for example in order to reduce the flow shearing force exerted on the cells by the nutrient liquid stream.

It is expedient if the clamping parts are constructed as clamping legs, which can be deformed away from each other elastically springing against the restoring force of their material. The holding clip or holding clamp is then constructed in an especially simple manner and can be constructed, for example, as a U-shaped clamp in cross-section and/or as a clamping rail. The clamping legs can be connected together as a single piece.

It is especially advantageous if the opposing contacts are affixed to the clamping part. The restoring force of the holding clip or holding clamp can then be used both for pressing the opposing contacts onto the connection contacts of the semiconductor chips, as well as for pressing the semiconductor chips against the seal located between them. Optionally, a conducting rubber can be provided on the clamping part of the mounting, which produces the electrical contact with the connection contacts located on the semiconductor chips.

A preferred, especially advantageous embodiment of the invention provides that the first semiconductor chip provided for the adherent deposit of the biological cells has at least one array with several planar sensors set apart from each other. The apparatus then allows a locationally resolved measurement on the individual cells of a cell culture adherently deposited on the active side of the semiconductor chip.

It is advantageous if at least one semiconductor chip has at least one micro-pump, which has at least one pump connection connected to an inlet channel or an outlet channel of the test chamber. Using the micropump, the nutrient medium, for example, can be conveyed into the test chamber.

Expediently, for tempering the test chamber, at least one semiconductor chip has an electronic heating unit integrated into the semiconductor chip or attached to it on its outer side facing away from the test chamber. This heating unit can have allocated to it, for example, on the active side of the semiconductor chip, a temperature sensor as well as a control device that may be integrated into the semiconductor chip, which regulates the temperature in the test chamber to a preset value, for example 37° C. The electronic heating unit can be, for example, a platinum meander vacuum metallized on the rear side of the semiconductor chip.

One embodiment of the invention provides that the apparatus has a transponder for transferring the measurement data to an external evaluation device. The measurement data can then be transmitted in a wireless manner to the evaluation device, such that the apparatus can be used better at locations which are difficult to access or are hermetically sealed. Also, the handling of the apparatus is then made easier.

It is especially advantageous if the two semiconductor chips arranged opposite each other are constructed identically. The apparatus can then be manufactured in an even more cost-effective manner.

A preferred embodiment of the invention provides that the first semiconductor chip has an optical window on whose inner side, facing the test chamber, biological cells are deposited adherently. The window then terminates with its inner side facing the test chamber preferably flush with the active area of the semiconductor chip having the planar sensors, so that a cell culture deposited on the active side of the semiconductor chip can extend over the optical window. It is thereby possible that during the measurements performed by the sensor, the biological cells can be observed, for example with a microscope or a camera. Additional information can thereby be obtained about the cells, which can possibly be correlated with the measurement values delivered by the sensors.

Through the window, the cells can instead be irradiated with light, for example with laser light, in order to stimulate them. The reaction of the cells can then optionally be tested using the sensors. Of course, the window can instead be used for other optical tests, for example spectral measurements. If the second semiconductor chip also has at least one optical window, a condenser lens can be applied to the window of the one semiconductor chip and an objective lens can be applied to the window of the other semiconductor chip. The test chamber can then be examined even better with a microscope.

One advantageous embodiment of the invention provides that on the active side of the first semiconductor chip, cells producing a biocatalyst are adherently deposited or depositable. Thus, for example, cells producing insulin are deposited onto the first semiconductor chip. The apparatus can then be implanted, for example, into a human or animal body, in order to produce insulin there for a long period of time. In this regard, the insulin can optionally be released into the body in a controlled manner using a micropump integrated into the apparatus. In an advantageous way, the vitality of the cells, and thus their ability to produce insulin, can be monitored using the sensors.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings, which are in part highly schematic.

and

Figure 5:
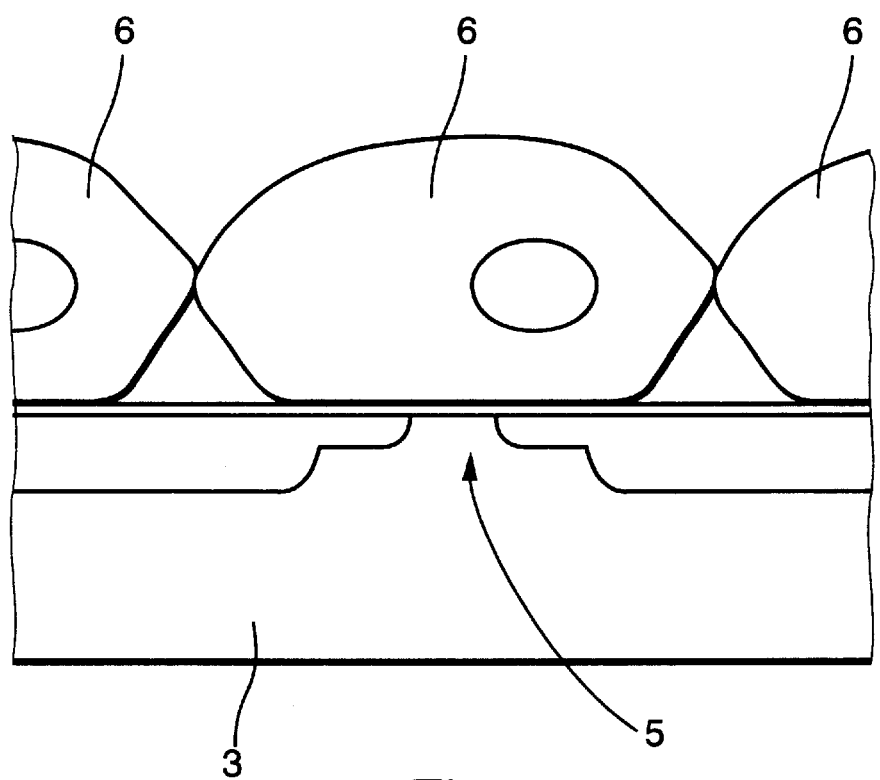

FIG. 5 is a partial cross-section through a semiconductor chip, on whose active flat side biological cells are deposited adherently.

DETAILED DESCRIPTION OF THE INVENTION

A apparatus indicated on the whole by 1 for measuring physiological parameters has a test chamber connected for a nutrient medium to an inlet opening and an outlet opening. The chamber is limited on the underside by a first semiconductor chip 3 and on the upper side by a second semiconductor chip 4. The semiconductor chip 3 arranged on the underside has on its active side facing the test chamber 2 a plurality of planar sensors 5, which are integrated into the substrate of the semiconductor chip 3 (FIG. 5). The semiconductor chip 3 has a flat surface on its active side.

Figure 2:
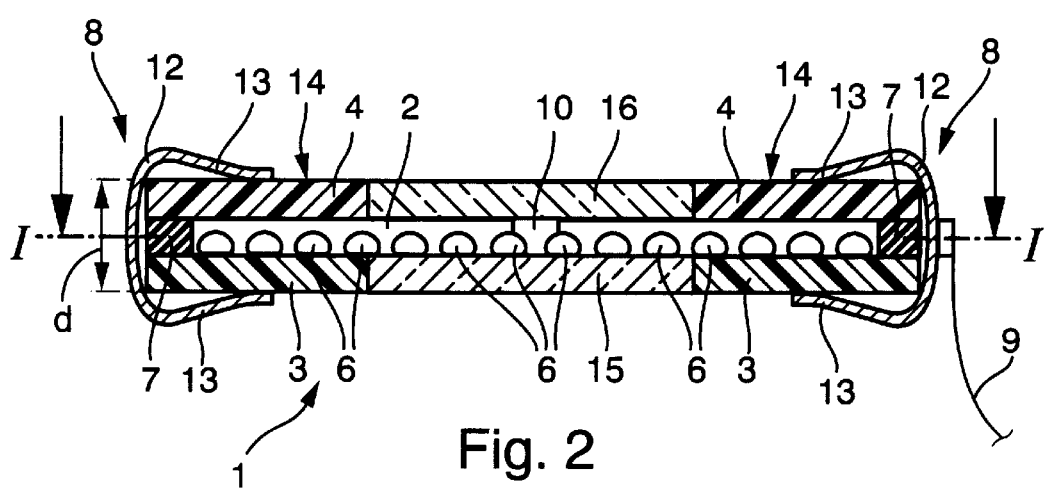
FIG. 2 is a cross-section through the plane indicated by II in FIG. 1, which makes it possible to recognize the measurement chamber with the cells located therein, which is bounded laterally by the sealing ring and, on the upper and lower sides, by respective semiconductor chips.
Figure 4:
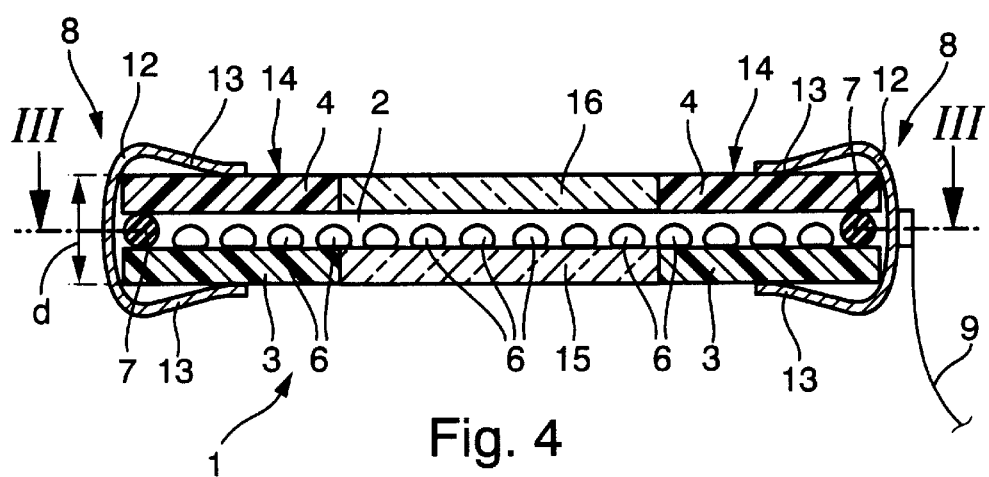
FIG. 4 is a view of the cross-sectional plane indicated in FIG. 3 by IV.

As can be easily recognized from FIGS. 2 and 4, biological cells 6, for example marine algae or fish gills, can be deposited in a nutrient medium on the active side of the semiconductor chip 3. The semiconductor chip 3 has for this purpose, on its flat side facing the test chamber 2, a surface structuring, whose roughness corresponds approximately to the coarseness of the cells to be deposited, so that they accept the semiconductor chip as neighbors. In FIG. 5, in the example of a planar sensor 5 integrated into the substrate of the semiconductor chip 3 and constructed as a field-effect transistor, it can be recognized that the cells 6 are arranged directly adjacent to the planar sensors 5. In this process, the distance between the cells and the active areas of the planar sensors typically amounts to approximately 20 nanometers. It is thereby possible to measure physiological parameters, for example ion concentrations, directly on the individual cells using the planar sensors 5.

Also, the second semiconductor chip 4 has an active side facing the test chamber 2. This side has several additional sensors, which are also constructed as planar sensors. Using the additional sensors, global physiological parameters can be measured in a nutrient medium contained in the test chamber 2.

Between the semiconductor chips 3, 4, a seal 7 is arranged as a distance spacer, which lies against both semiconductor chips 3, 4 and surrounds the test chamber 2. The semiconductor chips 3, 4 and the seal 7 located therebetween are held using a mounting 8 that grasps over the semiconductor chip 3, 4 on the outer side in the sealing position.

The semiconductor chips 3, 4 each have on their outer side facing away from the test chamber 2 electrical connection contacts, which contact with the opposing contacts of the mounting 8. For electrical connection of the two semiconductor chips 3, 4, the mounting 8 has connection lines connected to the opposing contacts, which are integrated into the mounting. For the power supply of the semiconductor chips 3, 4 and for the transfer of the measurement and control data, the mounting 8 has a connection for a connection cable 9 externally connected to the opposing contacts of the mounting 8.

On the whole, an apparatus 1 thus results, which is simple to construct and cost-effective in its manufacture, with which physiological parameters directly on the cells and global physiological parameters of the nutrient medium can be registered.

Figure 1:
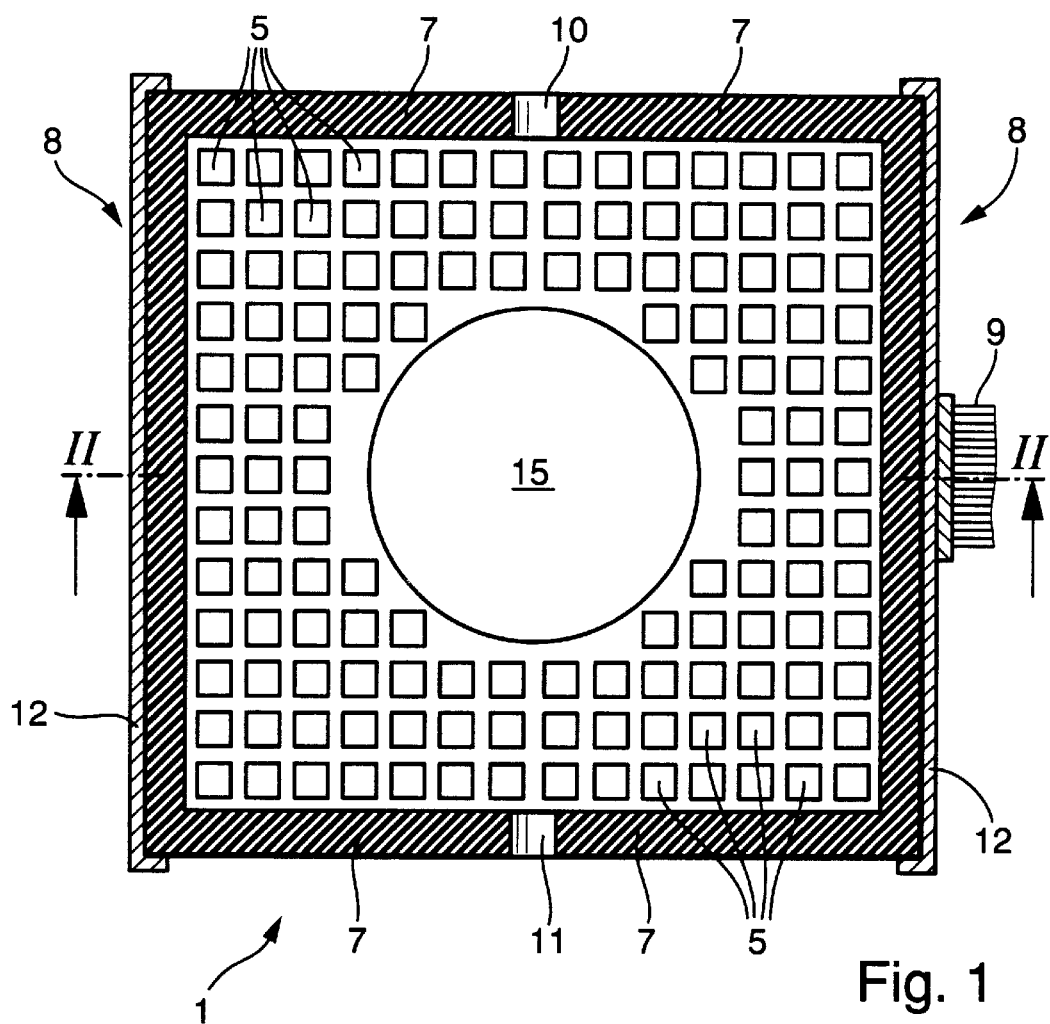
FIG. 1 is a plan view of the longitudinal central plane marked by I in FIG. 2, which makes it possible to recognize especially well the first semiconductor chip having the planar sensors, as well as the optical window inserted into it.

In the embodiments shown in FIGS. 1 and 2, the seal 7 is constructed as a silicone seal, which is penetrated by an inlet channel 10 and an outlet channel 11. Onto these a fluid treatment can be connected, for example, for renewing a nutrient medium contained in the test chamber 2. In the embodiment according to FIGS. 3 and 4, the seal is constructed as an elastic O-ring, which is penetrated by two hollow needles, which form the inlet and outlet channels 10, 11. The apparatus 1 can then be handled even better, whereby the hollow needles can be arranged differently depending on the application and/or can have various diameters.

The mounting 8 has two holding clamps 12 that are U-shaped in cross-section, each having two clamp legs 13, which have a smaller clearance distance in the starting position than the overall thickness d of the semiconductor chips 3, 4 to be clamped between the clamp legs 13 and which are spaced from each other by the seal 7. From the starting position the clamp legs 13 can be moved away from each other against the restoring force of their material. In this manner, the mounting 8 and the semiconductor chips 3, 4 can be combined with seals 7 having various thicknesses. Thus, depending on the measurement task, various clearance distances can be set between the semiconductor chips 3, 4, without modifications being necessary to the semiconductor chips 3, 4 or to the mounting 8 for this purpose. As seals, for example, O-rings can be provided which are commercially available in various sizes.

The opposing contacts are attached to the clamp legs 13 on the inside and, in the clamp position of the clamp legs 13, lie against the connection contacts, which are arranged on the outer flat sides of the semiconductor chips 3, 4 facing away from each other and are connected by throughplating to the planar sensors 5 or the additional sensors. The clamping force of the mounting 8 thus presses both the opposing contacts against the connection contacts, as well as pressing the semiconductor chips 3, 4 against the seal 7.

Figure 3:
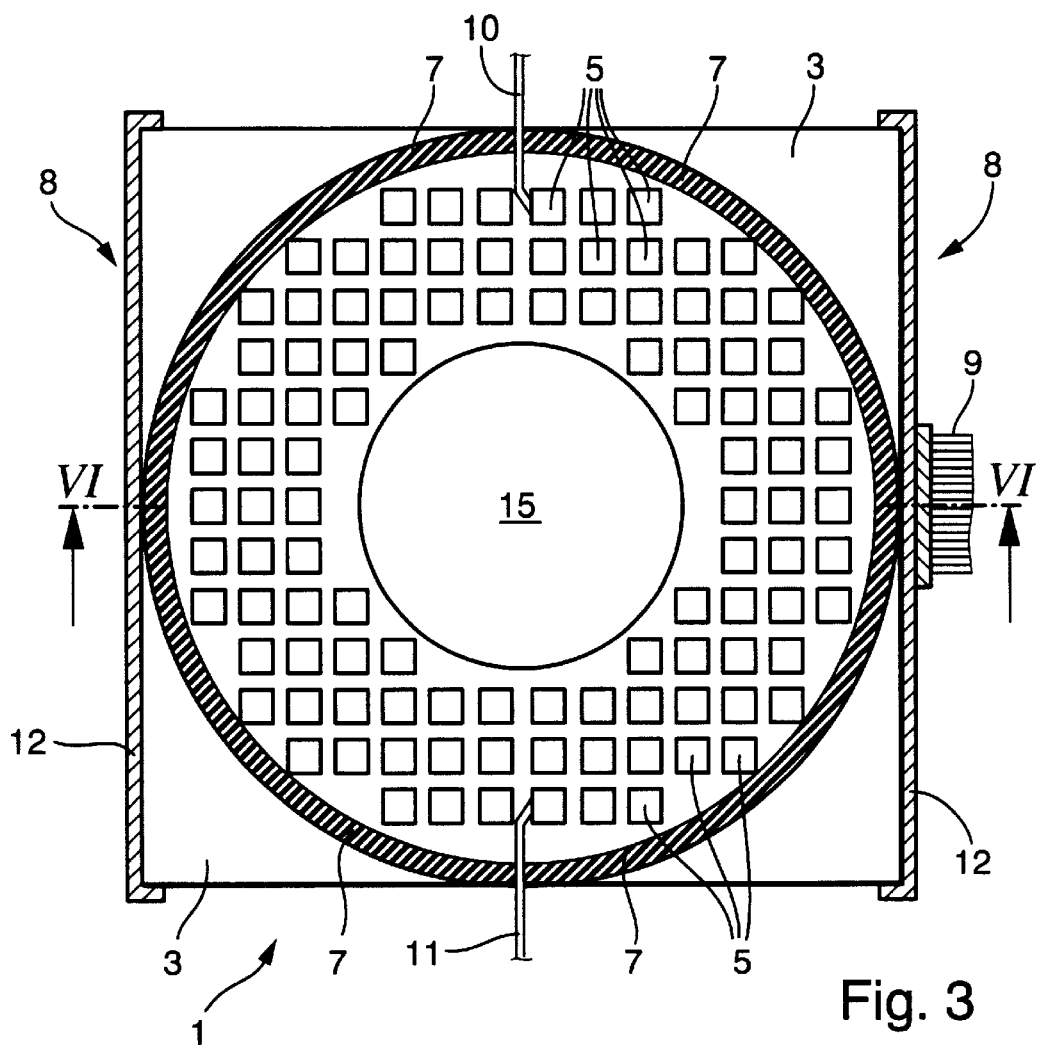
FIG. 3 is a representation similar to FIG. 1, wherein the seal is an elastic O-ring, through which hollow needles forming inlet channels and outlet channels have been stuck.

As can be recognized in FIGS. 1 and 3, the first semiconductor chip 3 provided for the adherent deposit of the biological cells 6 has an array with a plurality of planar sensors 5 spaced from each other. In order to measure different physiological parameters, the array has several respectively different planar sensors 5. The apparatus thereby makes possible a locally resolved measurement on the biological cells 6, wherein several different parameters can be registered at the same time.

As can be recognized in FIG. 1, the first semiconductor chip 3, adjacent to its active area having the planar sensors 5, has an optical window 15, which is inserted into a hole in the substrate of the semiconductor chip 3. The inner side of the window 15 facing the test chamber 2 forms a plane with the active inner side of the semiconductor chip 3, on which the biological cells 6 are adherently deposited. In FIGS. 2 and 4 it can be recognized clearly that a cell culture deposited onto the semiconductor chip 3 is deposited both on the active area of the semiconductor chip 3 and on the window 15. Using the windows 15, 16, cells located in the test chamber 2 can be examined with a microscope, in that for example, an objective lens is brought onto one of the windows 15, 16 and a condenser lens is brought onto the other window 16, 15.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. An apparatus for measuring physiological parameters, comprising a test chamber (2) connected to at least one inlet opening and at least one outlet opening and bounded by walls, wherein at least one wall of the test chamber (2) is constructed as a first semiconductor chip (3) having an active side with planar sensors (5) facing the test chamber (2), on which biological cells (6) located in a nutrient medium can be adherently deposited in order to measure physiological parameters directly on the cells (6), wherein at least one additional sensor is allocated to a wall lying opposite the first semiconductor chip (3) in order to measure global physiological parameters, the wall lying opposite the first semiconductor chip (3) being formed by a second semiconductor chip (4) having at least the one additional sensor on its active side facing the test chamber (2), wherein a seal (7) surrounds the test chamber (2) and forms a distance spacer between the semiconductor chips (3, 4), wherein the semiconductor chips (3, 4) are held in a sealing position using a mounting (8) that grasps over them on their outer side, and wherein the semiconductor chips (3, 4) each have electric connection contacts outside of the test chamber (2), which contact with opposing contacts of the mounting (8).

2. The apparatus according to claim 1, wherein at least one inlet channel (10) having the inlet opening and/or at least one outlet channel (11) having the outlet opening penetrates the seal (7).

3. The apparatus according to claim 1, wherein the seal (7) comprises an elastic material.

4. The apparatus according to claim 3, wherein the seal (7) comprises an O-ring.

5. The apparatus according to claim 1, wherein the mounting (8) has at least one holding clip (12) or a holding clamp with at least two clamping parts, which have a smaller clearance distance in a starting position than a total thickness (d) of the semiconductor chips (3, 4) spaced from each other by the seal (7) and to be clamped between the clamping parts, and wherein the clamping parts can be moved away from each other against a restoring force.

6. The apparatus according to claim 5, wherein the clamping parts are constructed as clamping legs (13), which can be deformed away from each other elastically springing against the restoring force of their material.

7. The apparatus according to claim 5, wherein the opposing contacts are attached to a clamping part.

8. The apparatus according to claim 1, wherein the first semiconductor chip (3) provided for the adherent deposit of the biological cells has at least one array with a plurality of planar sensors (5) spaced from each other.

9. The apparatus according to claim 1, wherein at least one of the semiconductor chip (3, 4) has at least one micro-pump, which has at least one pump connection connected to an inlet channel (10) or an outlet channel (1 1) of the test chamber (2).

10. The apparatus according to claim 1, wherein for tempering the test chamber (2), at least one of the semiconductor chips (3, 4) has an electronic heating unit integrated into the semiconductor chip (3, 4) or attached to it on its outer side facing away from the test chamber (2).

11. The apparatus according to claim 1, further comprising a transponder for transferring measurement data to an external evaluation device.

12. The apparatus according to claim 1, wherein the two semiconductor chips (3, 4) arranged opposite each other are constructed identically.

13. The apparatus according to claim 1, wherein the first semiconductor chip (3) has an optical window (15) on whose inner side, facing the test chamber (2), biological cells (6) are adherently deposited.

14. The apparatus according to claim 13, wherein the second semiconductor chip (4) has at least one optical window (16).

15. The apparatus according to claim 1, further comprising as a power supply, an electric energy storage unit and/or a solar cell and/or electrodes arranged on its outer side for galvanic power generation.

16. The apparatus according to claim 1, wherein on the active side of the first semiconductor chip (3) biological cells (6) producing a biocatalyst are adherently deposited.

* * * * *